US 6,610,307 B1

(12) United States Patent
Prideaux et al.

(10) Patent No.: US 6,610,307 B1
(45) Date of Patent: *Aug. 26, 2003

(54) IMMUNITY AGAINST *PASTEURELLA HAEMOLYTICA* LEUKOTOXIN

(75) Inventors: Christopher Thomas Prideaux, Coburg North (AU); Adrian Leslie Mark Hodgson, East Malvern (AU)

(73) Assignees: Commonwealth Scientific and Industrial Research Organisation, Campbell (AU); The State of Queensland Through its Department of Primary Industries, Queensland (AU); The State of New South Wales Through its Department of Agriculture, New South Wales (AU); The University of New England of Armidale, New South Wales (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,100

(22) PCT Filed: Nov. 1, 1996

(86) PCT No.: PCT/AU96/00685

§ 371 (c)(1),
(2), (4) Date: Jun. 23, 1998

(87) PCT Pub. No.: WO97/16531

PCT Pub. Date: May 9, 1997

(30) Foreign Application Priority Data

Nov. 2, 1995  (AU) ............................................. PN6313

(51) Int. Cl.⁷ ..................... A61K 39/102; A61K 39/02; A61K 39/295; A61K 39/116; A01N 63/00
(52) U.S. Cl. ................................ 424/255.1; 424/234.1; 424/235.1; 424/200.1; 424/201.1; 424/236.1; 424/203.1; 424/184.1; 424/93.4; 424/93.2; 435/69.3
(58) Field of Search ........................... 424/234.1, 184.1, 424/255.1, 256.1, 235.1, 200.1, 201.1, 236.1, 203.1, 93.4, 93.48, 93.2; 435/69.3, 71.1

(56) References Cited

U.S. PATENT DOCUMENTS

| 4,963,487 | A | * | 10/1990 | Schimmel ................. 435/172.3 |
| 5,165,924 | A | | 11/1992 | Shewen et al. |
| 5,422,110 | A | * | 6/1995 | Potter et al. .............. 424/255.1 |
| 5,885,589 | A | * | 3/1999 | Foged et al. .............. 424/255.1 |
| 6,180,112 | B1 | * | 1/2001 | Highlander et al. ...... 424/255.1 |

FOREIGN PATENT DOCUMENTS

| CA | 2045950 | * | 12/1992 |
| EP | 0400958 | * | 5/1990 |
| WO | WO 9106653 | * | 5/1991 |
| WO | WO 97/16532 | * | 5/1997 |

OTHER PUBLICATIONS

Spitznagel et al. Adv. Dent. Res. 9: 48–54, 1995 (abstract).*
Babiuk et al. Biotech. Adv. 12: 489–523, 1994.*
Conlon et al. Infect. Immun. 59: 587–591, 1991.*
Lally et al. J. Biol. Chem. 264: 15451–15456, 1989.*
Molecular Microbiology (1990), pp. 1933–1939, Cruz et al, "Deletion analysis resolves cell–binding and lytic . . . ".
Microbial Pathogenesis (1995), pp. 307–321, Guthmiller et al, "Mutational analysis of the putative leukotoxin transport . . . ".
Infection and Immunity (Mar. 1995), vol. 63, No. 3, pp. 1027–1032, Chidambaram et al, "Isolation of Pasteurella . . . ".
Veterinary Microbiology, (1991), pp. 147–158, Bhatia et al, "Factors involved in immunity against Actinobacillus . . . ".
J. Gen. Microiol. 130, (1984), pp. 2415–2426, Adam et al, "Purification, characterization, and immunological . . . ".
Bovine Pract. 3, (1982), pp. 26–30, Bennett, "Efficacy of Pasteurella bacterins for yearling feedlot heifers".
FEMS Micro. Rev. 88, (1992), pp. 137–162, Coote, "Structural relationships among the RTX determinants of Gram–negative . . . ".

(List continued on next page.)

Primary Examiner—S. Devi
(74) Attorney, Agent, or Firm—Jacobson Holman PLLC (57) ABSTRACT

Bovine respiratory disease (BRD) complex, shipping fever, or pneumomic pasteurellosis, is a multifactorial disease whereby a combination of viral infection, adverse environment and poor immune status may combine to predispose animals to bacterial infections. The exotoxin, or leukotoxin (Lkt), may contribute to pathogenesis by impairing the primary lung defenses and subsequent immune responses or by causing inflammations as a result of leukocyte lysis. The present invention provides a modified microorganism which produces an Lkt toxin, wherein said Lkt toxin is partially or fully inactivated. In a further embodiment of the present invention, there is provided a modified microorganism wherein an Lkt toxin operon including an Lkt structural gene and/or a post transational activator of the organism is partially or fully inactivated. The present applicants have found that a precursor of Lkt toxin has reduced toxic activity. Surprisingly, the Lkt toxin precursor is capable of inducing an immune response in an animal that offers cross protection against heterologous challenge with a microorganism which produces the Lkt toxin. A microorganism which naturally produces an Lkt toxin may be engineered to produce an inactive Lkt toxin precursor by eliminating the post-translational activator of the precursor product. Accordingly, in a preferred embodiment the microorganism is unable to produce a post-translational activator of the Lkt toxin precursor or produces an inactivated post-translational activator of the Lkt toxin precursor. The post-translational activator may be a product of the Lkt C gene.

19 Claims, 5 Drawing Sheets

OTHER PUBLICATIONS

Am J. Vet. Res. 44, (1983), pp. 981–985, Frank and Smith, "Prevalence of Pasteurella haemolytica in transported calves".

DNA 8, (1982), pp. 15–28, Gentry et al, "Serum neutralization of cytotoxin from Pasteurells haemolytica leukotoxin gene cluster".

Infection and Immunity 55, (1987), pp. 1987–1996, Lo et al, "Nucleotide sequence of the leukotoxin genes of Pasteurella . . . ".

Bovine Prac. 17, (1982), pp. 56–58, Morter et al, "Clinical evaluation of prophylactic regimens for bovine respiratory . . . ".

J. Immunol. Methods 135, (1990), pp. 277–280, McKimm–Breschkin, "The use of tetramethylbenzidine for solid phase immunoassays".

J. Clin. Microbiol. 24, (1986), pp. 218–222, Mosier et al, "Enzyme–linked immunosorbant assay for the detection of serum . . . ".

Infect. Immun. 57, (1989), pp. 711–716, Mosier et al, "Pasteurella haemolytica antigens sassociated with resistance to . . . ".

Vet Pathol. 15, (1978), pp. 313–321, Schiefer et al, "Correlation of microbiological and histological findings in . . . ".

Infect. Immun. 35, (1982), pp. 91–94, Shewen and Wilkie, "Cytotoxin of Pasteurella haemolytica acting on bovine . . . ".

Can. J. Vet. Res. 52, (1988), pp. 30–36, Shewen and Wilkie, "Vaccination of calves with leukotoxic culture supernatant . . . ".

J. Bact. 171, (1989), pp. 916–928, Strathde and Lo, "Cloning, nucleotide sequence, and characterization of genes encoding . . . ".

Gene 33, (1985), pp. 103–119, Yanisch–Perron et al, "Improved M13 phage cloning vectors and host strains; nucleotide . . . ".

Medline Abstract 2307519, C. Forestier et al, Infect. Immun., 58(3), pp. 828–832, 1990.

Medline Abstract 1419113, C. hughes et al, FEMS Microbiol. Immunol. 5(1–3), pp. 37–43, 1992.

Confer et al. Vet. Microbiol. 37: 353–368, 1993.*

* cited by examiner

ATCC
Lkt⁻
Lkt⁻ / 3B-Lkt

FIG 5

SEQUENCE LISTING

<160> NUMBER OF SEQ ID NOS: 2

<210> SEQ ID NO 1
<211> LENGTH: 36
<212> TYPE: DNA
<213> ORGANISM: Pasteurella haemolytica

<400> SEQUENCE: 1
cgcggatccc gggccatggg aactagactt acaacc                36

<210> SEQ ID NO 2
<211> LENGTH: 24
<212> TYPE: DNA
<213> ORGANISM: Pasteurella haemolytica

<400> SEQUENCE: 2
cgcgaattct taagctgctc tagc                24

IMMUNITY AGAINST *PASTEURELLA HAEMOLYTICA* LEUKOTOXIN

The present invention relates to modified microorganisms suitable for use as live vaccines. The present invention also relates to the use of modified microorganisms as biological vectors. The present invention further relates to vaccine compositions.

Bovine respiratory disease (BRD) complex, shipping fever, or pneumonic pasteurellosis, is a multifactorial disease whereby a combination of viral infection, adverse environment and poor immune status may combine to predispose animals to bacterial infections. BRD is a major cause of economic loss in the cattle feed lot industry. The principal microorganism associated with the disease is the bacteria *Pasteurella haemolytica* serotype 1. (Schiefer, et al., 1978). Under normal conditions *P. haemolytica* is a component of the normal flora of the upper respiratory tract, it is only when pulmonary clearance mechanisms are impaired that colonisation of the lung occurs resulting in disease (Frank and Smith, 1983). A number of virulence factors have been associated with *P. haemolytica*, including surface structures such as the capsular polysaccharide (Adam et al. 1984), and a secreted exotoxin which is heat labile and specific for ruminant leukocytes (Shewen and Wilkie, 1982).

The exotoxin, or leukotoxin (Lkt), may contribute to pathogenesis by impairing the primary lung defenses and subsequent immune responses or by causing inflammation as a result of leukocyte lysis. Characterisation of the Lkt has shown it to be a member of the RTX family of toxins (Strathdee and Lo, 1989) which are produced by a variety of bacteria including Actinobacillus spp, *Proteus vulgaris, Morganella morganii, Bordetella pertussis*, and the most characterised produced by *E. coli*. All RTX toxins function by producing pores in the target cells, thereby interrupting osmotic balance, leading to rupture of the target cell. Although the mode of action is identical for RTX toxins their target cells vary greatly in type and cross-species specificity. Structurally, this family of toxins are characterised by the presence of glycine rich repeat structures within the toxin that bind to calcium and may have a role in target cell recognition and binding, a region of hydrophobic domains that are involved in pore formation, the requirement for post translational activation, and dependence on a C-terminal signal sequence for secretion. Production and secretion of an active RTX toxin requires the activity of at least four genes, C, A, B, and D. The A gene encodes the structural toxin, the C gene encodes a post-translational activator and the B and D genes encode proteins that are required for secretion of the active toxin. The Lkt is encoded by an operon that consists of the four contiguous genes (CABD), transcribed by a single promoter. The Lkt differs from a number of other RTX toxins, which have a broad host cell specificity, by having a target cell specificity restricted to ruminant leukocytes (Reviewed: Coote, 1992).

The Lkt has also been associated with protective immunity; with anti-toxin antibodies in the field relating to disease resistance, and a commercial culture supernatant vaccine (Presponse; Langford Inc., Guelph, Ontario, Canada) containing Lkt showing efficacy in reducing the incidence and severity of pneumonia following experimental challenge and in the feed lot (Gentry et al., 1985; Mosier et al., 1986; 1989; Shewen and wlkie, 1987; Shewen et al., 1988). This culture supernatant vaccine, in addition to inducing anti-Lkt antibodies, also stimulates an immune response to other soluble antigens present in the culture supernatant, and therefore a direct correlation between anti-Lkt and protection can not be claimed.

The use of *Pasteurella bacterins* (inactive vaccines) in the field has had limited success in controlling pneumonic pasteurellosis, in several field trials the administration of bacterin based vaccine has not protected against disease or in some cases had led to an enhancement of disease (Bennett, 1982; Morter et al., 1982). Bacterin vaccines also have the disadvantages of requiring the use of adjuvants, may result in site reactions, and in a number of cases require multiple dose to obtain protection.

It is an object of the present invention to alleviate one or more of the problems of the prior art.

Accordingly, in one aspect the present invention provides a modified microorganism which produces an Lkt toxin, wherein said Lkt toxin is partially or fully inactivated.

The term "modified" includes modification by recombinant DNA techniques or other techniques such as chemical- or radiation-induced mutagenesis. Where recombinant DNA techniques involve the introduction of foreign DNA into host cells, the DNA may be introduced by any suitable method. Suitable methods include transformation of competent cells, transduction, conjugation and electroporation.

In a further embodiment of the present invention, there is provided a modified microorganism wherein an Lkt toxin operon including an Lkt structural gene and/or a post translational activator of the organism is partially or fully inactivated.

The term "Lkt toxin operon" as used herein the claims and description is intended to include those genes involved in the expression of an Lkt toxin being a product of the Lkt toxin operon. The genes included in the Lkt toxin operon include the post translational activator gene (C), the structural gene (A), and the B and D genes which encode proteins that are required for secretion of the activated Lkt toxin.

The term "partially or fully inactivated" as used herein the claims and description includes modification of a gene by recombinant DNA techniques including introduction and deletion of DNA from the gene including single or multiple nucleotide substitution, addition and/or deletion including full or partial deletion of the gene, using a target construct or plasmid segregation; and chemical induced-, radiation induced- or site specific mutagenesis.

The present applicants have found that a precursor of Lkt toxin has reduced toxic activity. Surprisingly, the present applicants have also found that the Lkt toxin precursor is capable of inducing an immune response in an animal that offers cross protection against heterologous challenge with a microorganism which produces the Lkt toxin.

Accordingly, in a preferred embodiment of the invention the inactivated Lkt toxin is a precursor of Lkt toxin. The precursor may be an unprocessed expression product of the Lkt structural gene. The Lkt structural gene may be the Lkt A gene.

The microorganism may be one which does not naturally produce an Lkt toxin. The microorganism may be a bacterium, virus or fungus into which the Lkt structural gene, such as the Lkt A gene, has been introduced.

In a preferred embodiment, however, the microorganism is one which naturally produces an Lkt toxin. The microorganism which naturally produces an Lkt toxin may be *Pasteurella haemolytica*.

The present applicants have found that a microorganism which naturally produces an Lkt toxin may be engineered to produce an inactive Lkt toxin precursor by eliminating the post-translational activator of the precursor product. Accordingly, in a preferred embodiment the microorganism is unable to produce a post-translational activator of the Lkt toxin precursor or produces an inactivated post-translational activator of the Lkt toxin precursor. The post-translational activator may be a product of the Lkt C gene.

In a preferred embodiment the Lkt C gene of the microorganism is inactivated or partially or fully deleted. The Lkt C gene may be inactivated by site specific mutagenesis. The Lkt C gene may be inactivated by any single or multiple nucleotide substitution, addition and/or deletion. Preferably, the Lkt C gene is inactivated by homologous recombination using a targeting construct. The targeting construct may include a selectable marker flanked by sequences homologous to sequences flanking the desired insertion site. The selectable marker may be a gene which confers resistance to a toxic substance such as mercury or may be an antibiotic resistance determinant. The antibiotic resistance determinant may be a gene coding for ampicillin resistance, kanamycin resistance or streptomycin resistance.

In some circumstances it may be undesirable to have a functional antibiotic resistance gene incorporated into a modified microorganism. Accordingly, the present invention contemplates a targeting construct which includes genetic elements, such as repeat sequences, which facilitate excision of the antibiotic resistance gene once the targeting construct has undergone homologous recombination with the host chromosome.

The present invention also contemplates a targeting construct which does not include a selectable marker. For example, the targeting construct may include a segment of the Lkt C gene which contains a deletion. Homologous recombination of the targeting construct with the host chromosome may result in the introduction of a deletion into the chromosomal Lkt C gene. Selection for recombinants may then be based on the absence of production of the Lkt toxin.

The targeting construct may be introduced directly into the host cell in a linear form. Alternatively, the targeting construct may be introduced via a suicide or non-replicating vector. The suicide vector may be any plasmid which does not replicate in the host microorganism. Microorganisms which naturally produce Lkt toxins are often non-permissive hosts for pEP vectors. Accordingly, pEP vectors are examples of suicide vectors which may be used in the present invention.

In another embodiment, site specific mutagenesis may be achieved by the technique of plasmid segregation. For example, a plasmid which contains a fragment of an Lkt C gene interrupted by a selectable marker gene may be introduced to a microorganism. The microorganism may be subsequently transformed with a second plasmid containing a second selectable marker gene. Host cells containing both plasmids may then be passaged through media which selects only for the second plasmid. Selection for the second plasmid may act against maintenance of the first plasmid. The first plasmid may, therefore, be lost, but in some cases recombination of the interrupted Lkt C gene fragment containing the selectable marker into the chromosome may occur. This process therefore may encourage recombination of the interrupted Lkt C gene into the chromosomal Lkt C gene, thus inactivating the chromosomal Lkt C gene.

In a further aspect of the present invention, there is provided an expression vector which encodes an Lkt toxin wherein said Lkt toxin is partially or fully inactivated, said vector encoding an Lkt toxin gene including an Lkt structural and/or post-translational activator gene wherein said Lkt toxin operon is partially or fully inactivated.

The term "expression vector" as used herein the claims and description includes a chromosomal or extrachromosomal element which is capable of expressing a DNA sequence including a foreign DNA sequence.

The Lkt A gene product may be expressed from a chromosomal Lkt A gene. The chromosomal Lkt A gene may be located in its natural position on the chromosome or may be inserted into the chromosome at a position other than its natural location. In addition, the Lkt gene product may be expressed from an Lkt A gene located on an extrachromosomal element such as a plasmid. In one embodiment, therefore, an extrachromosomal element containing an Lkt A gene may be introduced to a microorganism which has a functional chromosomal Lkt A gene and an inactivated chromosomal Lkt C gene. The Lkt A product expressed from the extrachromosomal element may supplement the Lkt A product expressed from the chromosomal gene.

Alternatively, the Lkt A gene product may be expressed entirely from an Lkt A gene or genes located on extrachromosomal elements such as plasmids. The Lkt A genes located on extrachromosomal elements may be expressed either in the presence or absence of selection for the extrachromosomal element. Thus, in one embodiment an extrachromosomal element containing an Lkt A gene may be introduced into a microorganism which lacks functional chromosomal Lkt A and Lkt C genes. The microorganism which lacks functional Lkt A and Lkt C genes may be produced by mutagenesis of the microorganism. The mutagenesis may result in deletion of the Lkt A and Lkt C genes or portions thereof.

The extrachromosomal element may be a recombinant expression vector which includes the Lkt A gene. Preferably the recombinant expression vector allows expression of the Lkt A gene in microorganisms which naturally produce Lkt toxins. The recombinant expression vector may allow expression of the Lkt A gene in *P. haemolytica*. The recombinant expression vector may be derived from a pIG plasmid. The recombinant plasmid may be derived from pIG3B. The recombinant plasmid may be pIG3B-Lkt.

Bacterial vector systems based on APP (Ph) provide an alternative means to deliver "naked DNA" vaccine molecules to host cells. Such naked DNA vaccine/expression systems would include a plasmid capable of replicating in the bacterial system, and a eukaryotic promoter controlling the expression of the foreign/recombinant gene of interest.

In a preferred embodiment the microorganism is able to produce one or more functional proteins which facilitate secretion of Lkt toxin molecules. The microroganism may have functional Lkt B and/or Lkt D genes. In another embodiment, the microorganism is unable to produce at least one of the proteins involved in secretion of Lkt toxin molecules or produces at least one inactive protein involved in secretion of Lkt toxin molecules. The microorganism may have an inactive Lkt B and/or Lkt D gene. Thus, the microorganism may be unable to secrete active or inactive Lkt toxin molecules.

In another aspect the present invention provides a vaccine composition for inducing an immunological response in a host animal inoculated with said vaccine composition, said vaccine composition including an Lkt toxin precursor. The Lkt toxin precursor may be an unprocessed expression product of an Lkt structural gene. The Lkt structural gene may be an Lkt A gene.

The present invention further provides a vaccine composition for inducing an immunological response in a host animal inoculated with said vaccine composition, said vaccine composition including a modified microorganism which produces an Lkt toxin, wherein said Lkt toxin is partially or fully inactivated. Preferably the inactivated Lkt toxin is a precursor of an Lkt toxin. The precursor may be an unprocessed expression product of an Lkt structural gene. The Lkt structural gene may be an Lkt A gene. Preferably, the microorganism is *Pasteurella haemolytica*. Preferably the Lkt C gene of the microorganism is inactivated or deleted.

In a preferred embodiment the vaccine composition which includes a modified microorganism is a live vaccine.

A vaccine composition of the present invention may be incorporated in any pharmaceutically acceptable vehicle with or without added adjuvants or immunostimulatory molecules.

The adjuvant may be of any suitable type. The adjuvant may be selected from vegetable oils or emulsions thereof, surface active substances, e.g., hexadecylamine, octadecyl amino acid esters, octadecylamine, lysolecithin, dimethyl-dioctadecyl-ammonium bromide, N,N-dicoctadecyl-N'-N' bis (2-hydroxyethyl-propane diamine), methoxyhexadecylglycerol, and pluronic polypols; polyamines, e.g., pyran, dextransulfate, poly IC, carbopol; peptides, e.g., muramyl dipeptide, dimethylglycine, tuftsin; immune stimulating complexes (ISCOMS); oil emulsions; and mineral gels and suspensions. A mineral suspension such as alum, i.e. aluminium hydroxide (Al(OH)$_3$), aluminum phosphate or aluminium sulphate is preferred. The adjuvant may be present in amounts of from approximately 1 to 75% by weight, based on the total weight of the vaccine composition.

It will be appreciated that a vaccine according to the present invention, which includes an Lkt toxin precursor or a microorganism capable of producing an Lkt toxin precursor, has the potential to provide protection against a range of serovars of a microorganism which produces the corresponding Lkt toxin.

In another aspect the present invention provides a biological vector including a *Pasteurella haemolytica* bacterium, wherein said bacterium has been modified such that it is incapable of producing an active Lkt toxin.

In a preferred embodiment, the modified bacterium is unable to produce a post-translational activator of the Lkt toxin precursor or produces an inactivated post-translational activator of the Lkt toxin precursor. The post-translational activator may be a product of an Lkt C gene. In a preferred embodiment the Lkt C gene of the modified bacterium is inactivated or deleted. The Lkt C gene may be inactivated by any single or multiple nucleotide substitution, addition and/or deletion.

The Lkt C gene may be inactivated by the introduction of a targeting construct containing a selectable marker into the Lkt C chromosomal gene through site specific recombination. The targeting construct may include genetic elements, such as repeat units, which facilitate excision of the antibiotic resistance gene once the targeting construct has undergone homologous recombination with the host chromosome. Alternatively, a targeting construct which does not contain a selectable marker may be used to introduce a deletion in the Lkt C chromosomal gene.

The term "biological vector" is used in its widest sense to include a biological means suitable for expression of biologically active molecules. The biological means is preferably a viable microorganism although dead organisms could be employed. The biological vector may be non-pathogenic or rendered avirulent or may be given in non-pathogenic or avirulent effective amounts. The term "biologically active molecules" includes functional molecules such as growth factors, hormones, enzymes, antigens or antigenic parts thereof, cytokines such as interleukins, interferons and tumor necrosis factors. The molecules may be expressed naturally by the biological vector. Alternatively, the molecules may be recombinant molecules expressed by transforming the biological vector with a plasmid carrying a gene or genes encoding the biologically active molecule and which is then expressed; or where the plasmid and/or gene or genes and/or parts thereof are integrated into the host genome, which includes the chromosome and/or any naturally or non-naturally occurring extra-chromosomal element, wherein the gene or genes or parts thereof are expressed.

It will be appreciated that a biological vector of the present invention may be used to provide one or more useful proteins to the host animal. The proteins so provided may act in synergy to bring about an enhanced reaction in the host animal. For example, the biological vector may produce an antigen in combination with a molecule which enhances an immunogenic response in the host animal to the antigen. The molecule which enhances the immunogenic response may be a cytokine.

It will also be appreciated that a biological vector of the present invention may be used to provide a multivalent vaccine. The term "multivalent vaccine" is used in its most general sense and extends to a modified microorganism capable of inducing an immune response to two or more distinct antigenic epitopes on or expressed by the modified microorganism where the two or more epitopes are indigenous to the modified microorganism. More commonly, however, a multivalent vaccine includea modified microorganism capable of inducing an immune response to virulent forms of said microorganism as well as to heterologous antigens expressed by said microorganism (such as recombinant antigens or those introduced by transduction, conjugation or transformation) and which are not indigenous to the microorganism. In this regard, a multivalent vaccine may be directed to two or more pathogenic agents. Preferred multivalent vaccines are those capable of inducing an immune response against an Lkt toxin and to at least one antigenic eptiope from one or more pathogenic agents. The pathogenic agents may be selected from bacterial pathogens such as Pasteurella spp., Haemophilus spp., Moraxella spp., Leptospira spp., Streptococcus spp., Salmonella spp., *E. coli*, Fusobacterium spp., Clostridium spp., Mycobactedum spp. The pathogenic agents may also be selected from endoparasites such as Haemonchus spp., Trichostrongylus spp., or ectoparasites such as Boophilus spp. Alternatively, the pathogenic agents may be selected from viral pathogens such as bovine viral diarrhoea virus (BVDV), parainfluenza virus (PI3), infectious bovine rhinotrachetis (IBR), coronavirus, rotavirus.

The present invention further provides a method of producing a modified organism which produces an Lkt toxin which is partially or fully inactivated which method includes providing a microorganism which produces an active Lkt toxin; and inactivating or deleting the Lkt C gene.

The present invention further provides a method of producing a modified organism which produces an Lkt toxin which is partially or fully inactivated which method includes providing a microorganism which is incapable of producing an active Lkt toxin; and introducing a functional Lkt A gene into said microorganism.

The invention in yet a further aspect provides a method for vaccinating an animal against an Lkt toxin producing microorganism, said method including administering to said animal an immunologically effective amount of a vaccine in accordance with the present invention.

The method of vaccination may be utilised in the treatment of production animals such as pigs, cattle, sheep, goats. The method of vaccination may also be used in the treatment of companion animals such as horses, dogs and cats. The method of vaccination may also be used in the treatment of humans. In a preferred embodiment the method of vaccination is utilized in the treatment of cattle. Preferably the method of vaccination is utilized in the treatment of bovine respiratory disease (BRD) complex.

Administration of a vaccine or vaccine vector in accordance with the present invention may be by any suitable route such as by oral or parenteral administration. The administration may be mucosal such as nasal or vaginal. Alternatively, administration may be intramuscular, intradermal, subcutaneous or intraperitoneal. The preparation may be in dry or liquid form. The route of administration chosen may also necessitate additional components such as protease inhibitors, anti-inflammatories and the like.

The invention in yet a further aspect provides a method for vaccinating an animal against a pathogenic organism, said method including administering to said animal an effective amount of a vaccine vector in accordance with the present invention wherein said vaccine vector synthesises an immunologically effective amount of an antigen of said pathogenic organism.

In yet another aspect the present invention provides a method for the production of an inactive Lkt toxin which method includes culturing a modified microorganism in accordance with the present invention and recovering the inactive toxin produced by said microorganism. The inactive Lkt toxin produced by this method may, for example, be used as the active immunogen in a vaccine for stimulating a protective immune response against an Lkt toxin.

Throughout the description and claims of this specification, the word "comprise" and variations of the word, such as "comprising" and "comprises", is not intended to exclude other additives, components, integers or steps.

In order that the invention may be more readily understood we provide the following non-limiting examples.

BRIEF DESCRIPTION OF THE FIGURES

FIG. 1. Construction of an Lkt expression cassette for *E. coli*. The Lkt gene was cloned into pQE, inframe with the poly HIS leader sequence to allow Lkt expression. The kanamycin resistance gene from pUC4K, was cloned into a unique XhoI restriction site 5' of the pQE-Lkt promoter/regulator sequences. The resulting plasmid, pQE-LktK, contains the Lkt gene under regulated expression, linked to the kanamycin resistance gene.

FIG. 3. Construction of an Lkt expression cassette for use in *P. haemolytica*. The Lkt expression cassette, linked to the kanamycin resistance gene, from pQE-LktK, was isolated as a SphII restriction enzyme fragment, treated with T4 DNA polymerase to generate blunt ends, and cloned into the unique EcoRV site of pIG3B. Not all unique restriction enzyme sites in the multiple cloning site of pIG3B are indicated.

FIG. 4. Western blot analysis of the Ph:Lkt$^-$ strain containing the Lkt expression cassette. Samples from exponentially growing cultures of *P. haemolytica* EMAI, Ph:Lkt$^-$, and the Ph:Lkt$^-$ strain containing the Lkt expression cassette (pIG3B-Lkt) were examined by western-blotting. Toxin bands were detected using rabbit antisera raised against the Lkt. The anti-Lkt sera bound to a polypeptide, corresponding in size to that of the Lkt in preparations of *P. haemolytica* strains EMAI, and Ph:Lkt$^-$/pIG3B-Lkt, but did not recognise a similar size band in the Lkt deficient stain Ph:Lkt$^-$.

FIG. 5. pIG Based Cassettes for the Expression of CAT in Ph. A series of pIG based expression cassettes were constructed for the expression of the CAT gene in Ph. Each plasmid had the same structure with the promoter aligned 5' of the CAT gene. The promoters used in the study were: the Ph Lkt promoter; the DNT promoter isolated from the dermonecrotic toxin of *Pasteurella multocida*; and the 
APX1 promoter isolated from the APX1 toxin of *Actinobacillus pleuropneumoniae*.

MATERIALS AND METHODS

Bacterial Strains and Growth Conditions

The *P. haemolytica* strains used in this study were obtained from the NSW Dept. Agriculture, Elizabeth Macarthur Institute, Menangle (EMAI; Australia), or the American Type Culture Collection (ATCC). Strains of *P. haemolytica* were grown in brain heart infusion broth (BHI) at 37° C. with continuous shaking. Blood agar were prepared by adding 5% sterile defibrinated sheep red blood cells to the BHI agar. Antibiotics were used at a final concentration of Kanamycin 25 µg/ml. The *E. coli* strain DH5α was used throughout this study, using standard techniques as outlined in Sambrook et al., (1989).

Isolation of *P. haemolytica* Genomic DNA

Bacteria present in 1 ml of an overnight culture of *P. haemolytica* EMAI, grown in BHI were collected by centrifugation, and the supernatant discarded. The pellet was resuspended in 1 ml of TE (10 mM Tris-HC1 pH8.5/1 mM EDTA), containing lysozyme (7.5 mg/ml), and incubated at 37° C. for 2 hr. After which the solution was adjusted to a final concentration of 0.1M MaC1, 1%SDS and 2.5 µg/ml ProteinaseK, and incubation continued overnight at 50° C. The following day the preparation was adjusted to 0.5M NaCl and extracted twice with phenol/chloroform/isoamyl alcohol (100:99:1, V/V/V), and the genomic DNA was then precipitated by the addition of 0.6 volumes of isopropanol.

Isolation and Cloning of the Lkt Gene

Amplification of the Lkt gene was performed using the polymerase chain reaction (PCR). Reactions were performed in 50 µl volumes comprising 50 ηg genomic DNA (EMAI), 3 ηg of oligonucloetide primer, 50 mMKCl, 10 mM Tris-HCl, pH8.3, 2.5 mM MgCl$_2$, 200 mg/ml BSA, 200 mM of each dATP, dCTP, dGTP and dTTP, plus 1 unit of Taq DNA polymerase (Perkin Elmer Cetus, USA).

Reactions were overlayed with an equal volume of paraffin oil and heated to 94° C. for 1 min, cooled to 55° C. for 2 min, and heated to 72° C. for 5 min. This cycle was repeated 35 times using a Perkin-Elmer-Cetus DNA thermal cycle. Specific oligonucleotides were designed based on the published sequence of the Lkt gene (Lo et al., 1987; Highlander et al., 1989). The sequence of the two oligonucleotides was 5' CGCGGATCCCGGGCCATGGGAACTAGACTTACAACC 3' (SEQ ID NO:1) and 5' CGCGAATTCTTAAGCTGCTCTAGC 3' (SEQ ID NO:2), and were designed to produce a PCR product with a BamH1 site at the 5' end and an EcoRI site at the 3' end to facilitate cloning. The oligonucleotides were synthesised using a gene Assembler Plus DNA Synthesiser (Pharmacia, Sweden). Products of PCR reactions, corresponding to the predicted molecular weight of the Lkt gene were isolated from agarose gels by gene cleaning (BRESATech, Australia), restriction enzyme digested with BamHI and EcoRI, and cloned into the corresponding sites of pUC18 (Yanish-Perron, et al., 1985), to form the plasmid pUC-Lkt. Confirmation of clones containing the Lkt gene was achieved by double stranded sequencing (results not shown).

Transformation of *P. haemolytica* with Plasmid DNA

Electrocompetent *P. haemolytica* were prepared by inoculating BHI broth with a single colony from and overnight BHI/blood agar plate. The culture was grown until an OD$_{600}$ of 0.8 was reached, at which time the culture was in mid-logarithmic growth (data not shown). Bacteria were harvested by centrifugation, and washed 3 times in 15% glycerol, and resuspended in 1/50 of the original volume. Aliquot's (50 µl) of electrocompetent *P. haemolytica* were transformed with plasmid DNA using the following conditions: 1000Ω, 2.25 kV and 25 µF, in 0.2 cm cuvettes. Following electroporation transformed cells were grown in BHI broth, with shaking at 37° C. for four hours, without antibiotic selection, before plating onto BHI agar containing the appropriate antibiotic selection.

Production of Antisera

The Lkt open reading frame derived by PCR was subcloned from pUC-Lkt into the expression vector pGEX2T, so as to be in frame with the GST gene. The GST-Lkt fusion protein was purified by GST affinity chromatography as per the manufacturers instructions (Pharmacia, Sweden).

Rabbits were given a total of three doses of purified protein (100 µg) at two week intervals, the first of which was in Freund's complete adjuvant, with subsequent vaccinations in Freund's incomplete adjuvant. Sera was collected two weeks following the final boost.

Western Blot Analysis

Wester, blot (immunoblot) analysis was performed by the method of Sambrook et al., (1989). Rabbit sera produced against the GST-Lkt fusion protein was used for detection of Lkt at a dilution of 1 in 50. The conjugate, used at a 1 in 1000 dilution, was Sheep anti-sera rabbit Ig affinity isolated HRP conjugated antisera (sienus) with tetramethylbenzidine (McKimm-Breschkin 1990) as the substrate. Bacterial samples for western blot analysis were prepared by diluting overnight cultures 1 in 20 in the appropriate growth media, and incubating at 37° C. with vigorous shaking until an OD$_{600}$ of 0.8 was reached. At this point samples containing 20 µl of total culture were analysed by SDS-PAGE, and proteins transferred to nitrocellulose (Bio-Rad) using a Bio-Rad Transblot Cell as described in the manufacturer's specifications.

Construction of an Lkt Expression Cassette for *P. haemolytica*

Figure 1:
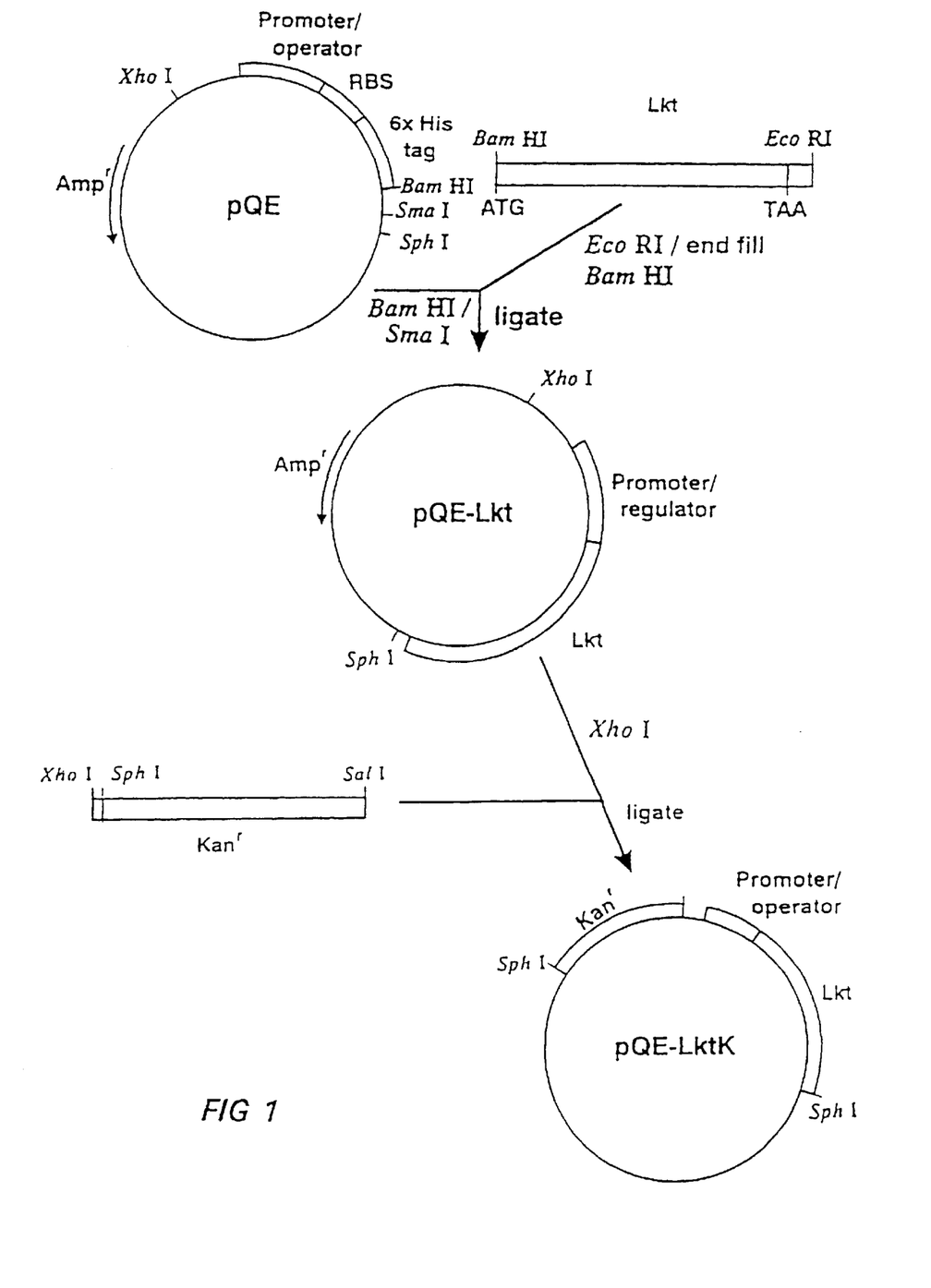

The Lkt open reading frame (ORF) was subcdoned from pUC-Lkt into the expression vector pQE30 (IQAGEN Inc., Chatsworth, Calif., USA) in frame with the poly-His purification signal, as outlined in FIG. 1. Expression of the Lkt gene from pQE30 (pQE-Lkt) was under the control of the *E. coli* phage T5 promoter and two lac operator sequences. To facilitate the sub-cloning of this expression element from pQE-Lkt to alternative plasmids the Kanamycin resistance gene was isolated from pUC4K (Pharmacia) and shuttled through pIC20R before being cloned into pQE-Lkt as outlined in FIG. 1. The resulting plasmid, pQE-LktK, contains the Kanamycin resistance gene and Lkt gene, linked to the T5 promoter, both flanked by unique SphI restriction enzyme sites (FIG. 1).

Figure 2A:
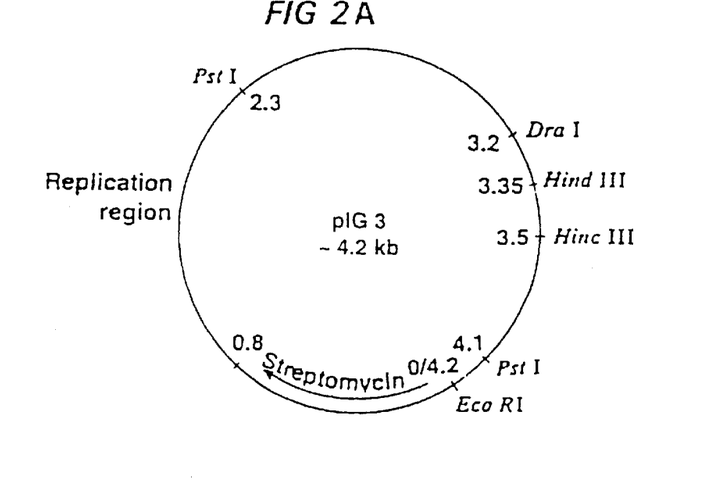
FIGS. 2A–2C. Partial restriction enzyme map of pIG3 (FIG. 2A), a 4.2 kb plasmid encoding streptomycin resistance, isolated from an Australian strain of *Actinobacillus pleuropneumoniae*. A 2.3 kb PstI. fragment (pIG317) was found to be sufficient to encode plasmid replication and confer streptomycin resistance when self ligated, and transformed into *E. coli* or *P. haemolytica*. The plasmid vector pIG3B, containing a multiple cloning site (MCS) and a portion of the lac gene, was constructed by introducing the HaeII fragment of pIC19R into the unique EcoRI site of pIG317 (FIG. 2B). Unique restriction enzyme sites are indicated for pIG3B (C), with the exception of PstI which cuts in the MCS and plasmid backbone (FIG. 2C).
Figures 2B, 2C:
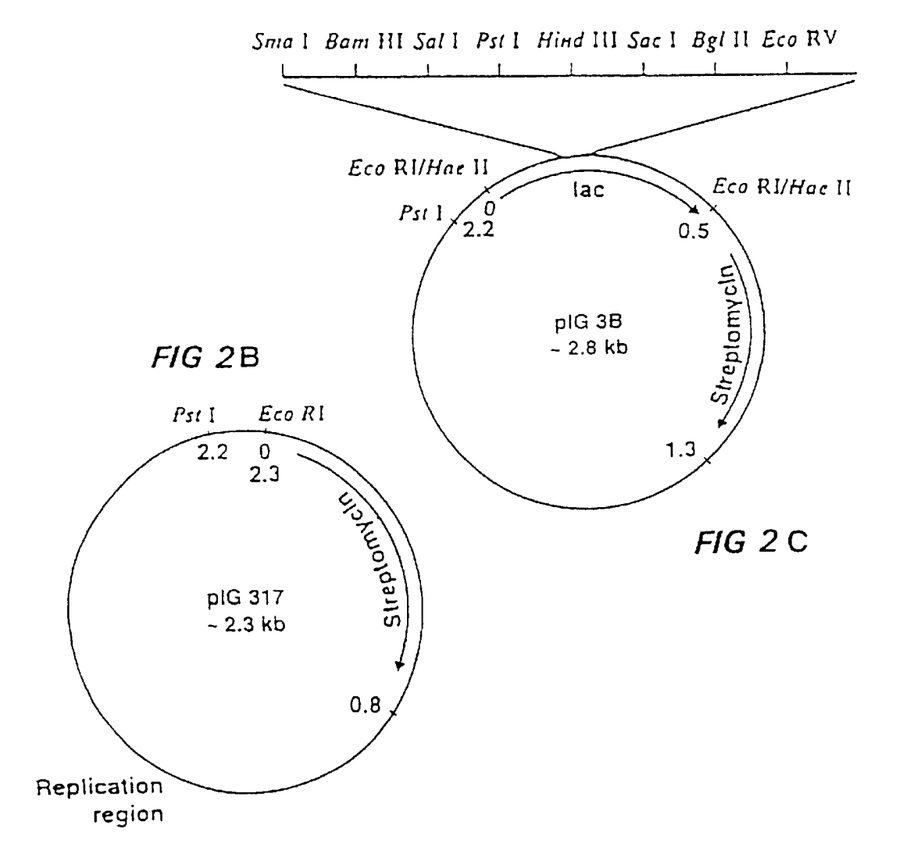
Figure 3:
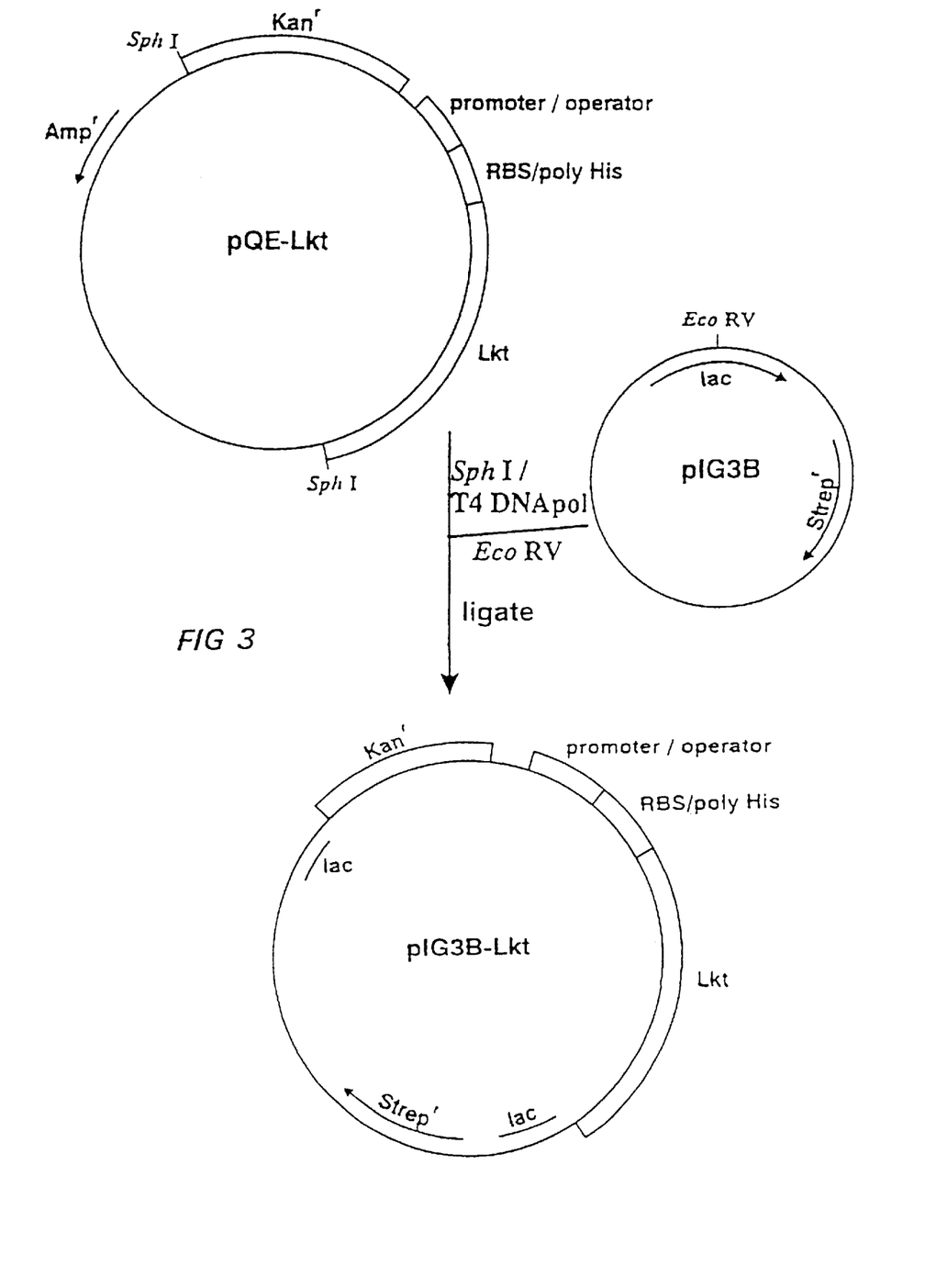

A plasmid suitable for transforming *P. haemolytica* has been developed within our laboratory. The parent plasmid was isolated from an Australian strain of *Actinobacillus pleuropneumoniae* and has been developed into the plasmid vector pIG3B as outlined in FIGS. 2A, 2B and 2C. The SphI restriction enzyme fragment containing the Lkt gene, and the transcription regulation signals, was isolated from pQE-T1K, and subcloned into the EcoRV site of pIG3B to produce the *P. haemolytica* Lkt A gene expression vector pIG3B-Lkt, as outlined in FIG. 3.

Construction of *P. haemolytica* Vaccine Strain

During a process of site mutagenesis of the *P. haemolytica* (EMAI strain) chromosome, designed to delete a small portion of the Lkt C gene, an isolate was obtained that failed to produce a zone of haemolysis on blood agar plates. Further characterisation of this strain (Ph:Lkt⁻) showed it to be deficient in both Lkt C and A production.

The Ph:Lkt⁻ strain was transformed with pIG3B-Lkt as described in materials and method, and DNA was isolated from Kanamycin resistance colonies and analysed by restriction enzyme digestion to confirm the predicted profiles of pIG3B-Lkt.

Characterisation of the *P. haemolytica* Vaccine Strain

Overnight cultures of Ph:Lkt$^{31}$ strain containing pIG3B-Lkt, as well as the *P. haemolytica* Ph:Lkt⁻, and ATCC strains, were examined by western blotting using antisera raised in rabbits against the GST affinity purified Lkt protein. From the western blot (FIG. 4) it can be seen that the Ph-Lkt⁻ strain did not specifically bind any antibodies present in the sera, whilst both the wild type ATCC strain and the Ph:Lkt⁻ strain containing pIG3B-Lkt both produced proteins of the predicted molecular weight of the Lkt, that reacted with the Lkt antiserum.

EXAMPLE 1

EVALUATION OF PH TOX: VACCINE STRAIN IN CATTLE

Cattle, at approximately 1 year of age, were bled prior to use to confirm the absence of pre-existing antibodies to Ph, after which they were distributed into two random groups of three. On day 0 one group of three received 50 ml of an exponentially growing culture of Ph-Lkt (equivalent to $5 \times 10^{10}$ c.f.u.) via intra-tracheal inoculation. Prior to the vaccination experiment, experiments had been carried out where cattle were given doses of the Ph-Lkt⁻ vaccine strain ranging from $5 \times 10^{10}$ to $2 \times 10^{11}$, and monitored for clinical signs and autopsied 1 week post-challenge to determine if lung lesions had developed. At all doses tested no lung lesions were evident and cattle did not display temperatures outside the normal range. The second group served as unvaccinated controls. On day 14 cattle were revaccinated as per day 0. On day 28 all cattle were challenged with 100 ml of an exponentially growing culture of wild type Ph (equivalent to $1 \times 10^{11}$ c.f.u.) by direct inoculation into the trachea. Clinical signs were monitored for the next 8 days, at which time all cattle were euthanaised and lung lesions scored.

The number and severity of lung lesions present in each animal upon autopsy, 8 days post-challenge, are presented in Table 1. Challenge of the unvaccinated controls with Ph resulted in acute pneumonia in 2 of the 3 cattle challenged. The third animal showed no signs of Ph infection upon autopsy, possibly resulting from an error in delivering the challenge via the trachea, or alternatively, as Ph is a commensal in a large number of cattle, this animal may have developed immunity to Ph prior to challenge. Within the vaccinated group of animals only one developed any sign of Ph infection. This was in the form of several lobules of consolidation (less than 1 cm in size) in the right apical lobe.

Figure 4:
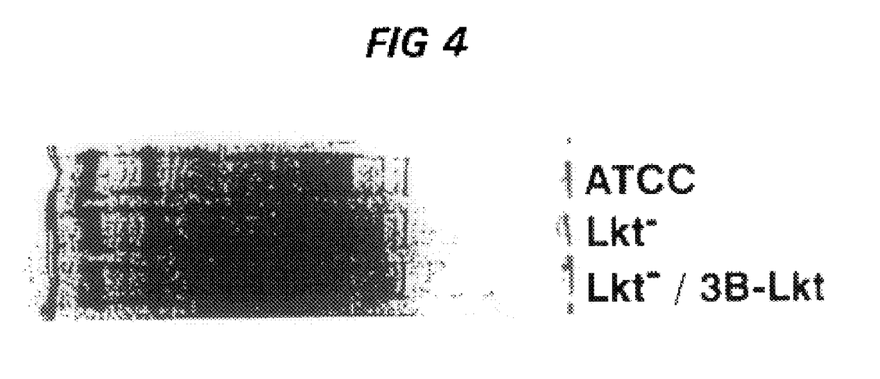

This experiment clearly demonstrates the potential of Ph-Lkt⁻ to be used as a live vaccine to protect cattle against Ph induced BRD. It was found that challenge with the Ph-Lkt⁻ strain does not induce lesions in the lungs of cattle (up to a dose of $10^{11}$ c.f.u.), and therefore the vaccine strain would not detrimentally affect cattle. In experiments undertaken to determine the most appropriate challenge dose, challenge with wild type Ph at three times the dose used in this experiment resulted in death of the animal (3 out of 3 animals) in less than 48 hours. Even with an extreme challenge $1 \times 10^{11}$ c.f.u., only one of the vaccinates showed any sign of Ph infection, and this was at a much reduced level to that seen in two out of three unvaccinated controls. Further characterisation of lesions in this animal showed it to be of chronic form, greater than 8 days of age (i.e. present before challenge). The Ph isolated from this lesion were found to produce Lkt and therefore were not the vaccine strain. Possibly this lesion resulted from the establishment of an opportunistic, wild type, Ph injection during vaccination. Although one animal developed minor signs of Ph infection of the Ph-Lkt⁻ strain, it is reasonable to conclude that expression of an inactive form of the Lkt, known to have a role in protective immunity, from this strain would increase the levels of protection obtained. The potential to express inactive forms of the Lkt from this strain has been demonstrated elsewhere in this document (FIG. 4).

Expression of Foreign Proteins from Ph Vectors

The potential to express recombinant genes from Ph was demonstrated earlier in this document where the Lkt gene was expressed, from a plasmid, within the Ph Tox⁻ strain. The Lkt expressed from the plasmid was seen to react with antisera generated against the Lkt in western blots (FIG. 4). In addition to expression of the Lkt from Ph, it is also possible that additional antigens could be expressed from a Ph strain, that had first been rendered avirulent through modification of the Lkt operon, to generate multivalent vaccines.

Figure 5:
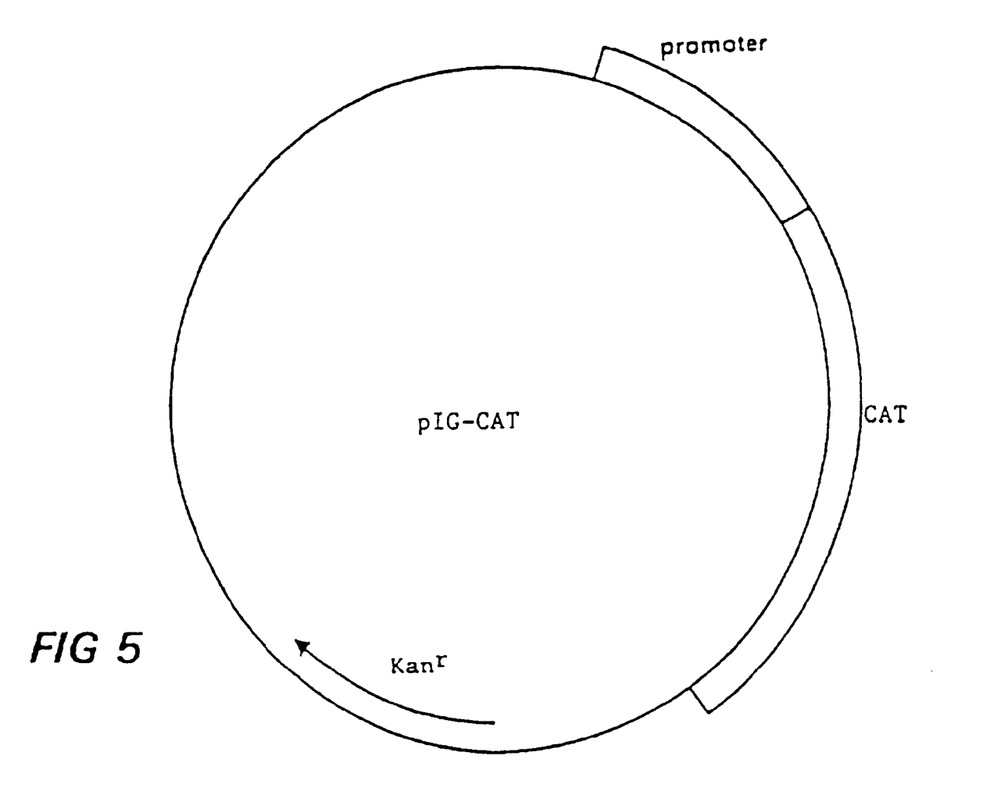

To further demonstrate the potential of Ph to act as a bacterial vector, a series of pIG based expression cassettes (FIG. 5) were constructed in which a number of promoters were used to drive the expression of the chloramphenicol acetyl transferase (CAT) gene. The CAT gene encodes an enzyme that offers resistance to the antibiotic chloramphenicol, and is easily quantitated in enzyme reactions. The promoters used to drive the expression of the CAT gene in Ph were isolated, within our laboratory, from various bacteria belonging to the Pasteurellaceae family. The various promoter/CAT cassettes (pIG-CAT) were constructed in 
E.coli and then transformed into Ph as described in materials and methods. Plasmid DNA was isolated from antibiotic resistant colonies and analysed by restriction enzyme digestion to confirm the predicted profiles. All Ph strains transformed with the CAT expression cassettes were found to be resistant to the antibiotic chloramphenicol. Levels of CAT activity expressed by each construct were quantitated in enzyme assays.

A sample of an exponentially growing culture of Ph/pIG-CAT was pelleted, and the bacteria resuspended in Tris pH8.0. Soluble proteins were isolated from bacteria by sonication and centrifugation, and the extract used in CAT assays, CAT enzyme assays contained 150 µl of reaction buffer (Chloramphenicol 1 mg/ml, $^3$H-CoA 0.1 µl/150 µl (Amersham International), Tris pH8.0) and 50 µl of protein extract. Reactions were allowed to proceed for 30 min and the level of CAT enzyme activity estimated by scintillation counting, using Econoflur (Dupont) scintillation fluid. CAT enzyme reactions are based on the transfer of the $^3$H group from a substrate insoluble in organic solvents (scintillation fluid), to an organic soluble product by the CAT enzyme. All promoters evaluated were found to be suitable to achieve foreign gene expression within Ph, with CAT levels obtained significantly above back ground levels (Table 2) for all Ph/pIG-CAT constructs.

The development of Ph as a bacterial vector system will enable foreign proteins, of commercial significance, to be delivered to the mucosal of cattle. The type of protein that could be delivered includes cytokines, that control and regulate the immune system, which would serve to non-specifically up-regulate the immune system. The vectored molecule(s) could also be protective antigens from other pathogenic bacteria, providing the potential to construct multi-valent vaccines. Such vaccines would have the potential to offer protection from more than one disease following a single vaccination.

TABLE 1

Lung Lesions Present in Cattle on Autopsy
Cattle were vaccinated twice with Ph-Lkt at two week intervals, and challenged with wild type Ph two weeks following the final vaccination. Post mortems were performed 8 days post-challenge and lung lesions recorded.

| | |
|---|---|
| Group 1 | Unvaccinated and Challenged |
| 1. | No sign of Ph infection |
| 2 & 3. | Acute pneumonia and consolidation of right apical lung lobe<br>Acute adhesive pleuritis. One animal also had a localised adhesion between the right diaphragmatic lobe and the pericardium. |
| Group 2 | Vaccinated and Challenged |
| 1 & 2 | No sign of Ph infection |
| 3. | Several lobules, of less than 1 cm in right apical lobe.<br>(lesions chronic, greater than 8 days of age) |

TABLE 2

Expression of the CAT Gene within Ph
Ph was transformed with various promoter/CAT constructs and the level of CAT gene expression estimated using enzyme reactions. Results are expressed as counts per 30 seconds. Tris served as a negative control to measure spontaneous break down of CAT substrate.

| Promoter | CAT Activity |
|---|---|
| No Promoter | 200 |
| Lkt | 29,300 |
| APX1 | 40,000 |
| DNT | 44,500 |

Finally, it is to be understood that various alterations, modifications and/or additions may be introduced into the constructions and arrangements of parts previously described without departing from the spirit or ambit of the invention.

REFERENCES

Adam, C., Knights, J. M., Mudridge, A., Lindon, J. C., Baker, P. R. W., Beesley, J. E., Spacey, B., Carig, G. R., and Nagy, L. K. (1984) Purification, characterization, and immunological properties of serotype-specific polysaccharide of *Pasteurella haemolytica* (serotypeA1) organisms. J. Gen. Microbiol. 130:2415–2426.

Bennett, B. W., (1982). Efficacy of *Pasteurella bacterins* for yearling feedlot heifers. Bovine Pract. 3:26–30.

Coote, J. G., (1992). Structural relationships among the RTX determinants of Gram-negative bacteria. FEMS Micro. Rev. 88:137–162.

Frank, G. H., and Smith, P. C., (1983). Prevalence of *Pasteurella haemolytica* in transported calves. Am J. Vet. Res. 44:981–985.

Gentry, M. J., Confer, A. W., and Panceirta, R. J., (1982). Serum neutralization of cytotoxin from *Pasteurella haemolytica* leukotoxin gene cluster. DNA 8:15–28.

Lo, R. Y. C. Strathdee, C. A., and Shewen, P. E., (1987). Nucleotide sequence of the leukotoxin genes of *Pasteurella haemolytica* A1. Infection and Immunity. 55:1987–1996.

Morter, R. L., Amstutz, H. E., Crandell, R. A., (1982). Clinical evaluation of prophylactic regimens for bovine respiratory disease. Bovine Prac. 17:56/58.

McKimm-Breschkin, J. L., (199). The use of tetramethylbenzidine for solid phase immunoassays. J. Immunol. Methods 135:277–280.

Mosier, D. A., Confer, A. W., Hall, S. M., Gentry, M. J. and Panciera, R. J., (1986). Enzyme-linked immunosorbant assay for the detection of serum antibodies to *Pasteurella haemolytica* cytotoxin (leukotoxin) in cattle. J Clin. Microbiol. 24:218–222.

Mosier, D. A. Simons, K. R., Confer, A. W., Panciera, R. J., and Clinkenbeard, K. D., (1989). *Pasteurella haemolytica* antigens associated with resistance to pneumoic pasteurellosis. Infect. Immun. 57:711–716.

Sambrook, J., Fritsch, E. F., and Maniatis, T., (1989). Molecular cloning: a laboratory manual, 2nd Ed. Cold Spring Harbour Laboratory Press, Cold Spring Harbour, N.Y.

Schiefer, B., Ward, G. E. and Moffaft, R. E., (1978) Correlation of microbiological and histological findings in bovine fibrinous pneumonia. Vet Pathol. 15:313–321.

Shewen P. E. and Wilkie B. N., (1982) Cytotoxin of *Pasteurella haemolytica* acting on bovine leukocytes. Infect, Immun. 35_91–94.

Shewen, P. E. and Wilkie B. N., (1987) Vaccination of calves with leukitoxic culture supernatant from *Pasteurella haemolytica* Can. J. Vet. Res. 52:30–36.

Stratthdee, A. A. and Lo, R. Y. C., (1989) Cloning, nucteotide sequence, and characterisation of genes encoding the *Pasteurella haemolytica* leukotoxin determinant. J. Bact 171:916–928.

Yanisch-Perron, C. Vieira, J., and Messing, J., (1985). Improved M13 phage cloning vectors and host strains; nucleotide sequence of the M13 mp18 and pUC19 vectors. Gene 33:103–119.

What is claimed is:

1. A genetically modified *Pasteurella haemolytica*, which (i) produces and secretes an inactive leukotoxin (Lkt toxin) precursor, without producing Lkt toxin, and (ii) induces in a bovine or ovine host animal a protective immune response to *Pasteurella hemolytica* that naturally produces an active Lkt toxin.

2. The genetically modified *Pasteurella haemolytica* according to claim 1 which is obtained from said *Pasteurella haemolytica* which naturally produces the Lkt toxin and the Lkt toxin precursor and which contains in its natural position on the chromosome: a) an Lkt toxin operon comprising a post-translational activator gene encoding a post-translational activator that activates the Lkt toxin precursor; b) an Lkt structural gene encoding the Lkt toxin precursor; and c) two genes encoding proteins necessary to secrete the Lkt toxin, by a genetic modification comprising site-specific mutagenesis of the post-translational activator gene to produce the genetically modified *Pasteurella haemolytica*, which produces no post-translational activator.

3. The genetically modified *Pasteurella haemolytica* according to claim 1, wherein the Lkt toxin precursor is an unprocessed expression product of an Lkt structural gene.

4. The genetically modified *Pasteurella haemolytica* according to claim 2, wherein the Lkt toxin precursor is an unprocessed expression product of said Lkt structural gene.

5. The genetically modified *Pasteurella haemolytica* according to claim 2, wherein the Lkt toxin precursor is encoded by Lkt A gene.

6. The genetically modified *Pasteurella haemolytica* according to claim 2, wherein the post-translational activator gene is partially or fully deleted.

7. The genetically modified *Pasteurella haemolytica* according to claim 2, wherein the post-translational activator gene is an Lkt C gene.

8. The genetically modified *Pasteurella haemolytica* according to claim 2, wherein the post-translational activator gene is modified by a recombinant DNA technique, chemically induced site-specific mutagenesis, or radiation-induced site-specific mutagenesis.

9. The genetically modified *Pasteurella haemolytica* according to claim 8, wherein the recombinant DNA technique is (i) single or multiple nucleotide substitution, addition, and/or deletion, (ii) homologous recombination using a target construct, or (iii) plasmid.

10. The genetically modified *Pasteurella haemolytica* according to claim 2, wherein the structural gene is modified by a recombinant DNA technique, chemically induced site-specific mutagenesis, or radiation-induced site-specific mutagenesis.

11. The genetically modified *Pasteurella haemolytica* according to claim 10, wherein the recombinant DNA technique is (i) single or multiple nucleotide substitution, addition, and/or deletion, (ii) homologous recombination using a target construct, or (iii) plasmid segregation.

12. A vaccine composition for inducing a protective immune response to a *Pasteurella haemolytica* that naturally produces an active Lkt toxin in a bovine or ovine host animal, said vaccine composition comprising:

a) the genetically modified *Pasteurella haemolytica* according to claim 1 in combination with b) a pharmaceutically acceptable vehicle.

13. A vaccine composition for inducing a protective immune response to a *Pasteurella haemolytica* that naturally produces an active Lkt toxin in a bovine or ovine host animal, said vaccine composition comprising a) the genetically modified *Pasteurella haemolytica* microorganism according to claim 2 in combination with b) a pharmaceutically acceptable vehicle.

14. A biological vector comprising the genetically modified *Pasteurella haemolytica* according to claim 1.

15. The biological vector according to claim 14, which further expresses a biologically active molecule.

16. The biological vector according to claim 15, further comprising a plasmid incorporated into said genetically modified *Pasteurella haemolytica* microorganism, said plasmid carrying a gene encoding the biologically active molecule.

17. A biological vector comprising the genetically modified *Pasteurella haemolytica* according to claim 2.

18. The biological vector according to claim 17, which further expresses a biologically active molecule.

19. The biological vector according to claim 18, further comprising a plasmid incorporated into said genetically modified *Pasteurella haemolytica*, said plasmid carrying a gene encoding the biologically active molecule.

* * * * *